United States Patent [19]

Wie et al.

[11] Patent Number: 5,240,844
[45] Date of Patent: * Aug. 31, 1993

[54] TEST KIT FOR DETERMINING THE PRESENCE OF ORGANIC MATERIALS AND METHOD OF UTILIZING SAME

[76] Inventors: Siong I. Wie, 4542 Wyngate Cir., Irvine, Calif. 92714; Arden A. Kelton, 414 Greenfern Ct., Burlington, N.C. 27215

[*] Notice: The portion of the term of this patent subsequent to Feb. 13, 2007 has been disclaimed.

[21] Appl. No.: 167,713

[22] Filed: Mar. 14, 1988

Related U.S. Application Data

[63] Continuation-in-part of Ser. No. 775,991, Sep. 13, 1985, U.S. Pat. No. 4,900,663.

[51] Int. Cl.⁵ .................. G01N 33/543; G01N 33/558
[52] U.S. Cl. ................... 435/7.92; 422/56; 422/58; 435/805; 435/810; 436/514; 436/518; 436/807; 436/809
[58] Field of Search ............... 422/56, 58; 435/7, 805, 435/810; 436/514, 518, 807, 809

[56] References Cited

U.S. PATENT DOCUMENTS

| | | | |
|---|---|---|---|
| 3,791,433 | 2/1974 | Moyer et al. | 435/810 |
| 3,811,840 | 5/1974 | Bauer et al. | 435/14 |
| 4,366,241 | 12/1982 | Tom et al. | 435/805 |
| 4,666,863 | 5/1987 | Edwards et al. | 436/536 |

OTHER PUBLICATIONS

Giegel et al, *Clinical Chemistry*, 28, 1894-1898, 1982.

*Primary Examiner*—Esther M. Kepplinger
*Assistant Examiner*—David A. Saunders
*Attorney, Agent, or Firm*—Sigalos, Levine & Montgomery

[57] ABSTRACT

A test card incorporates a colorimetric indicator test to determine the presence of a minute amount of a specific substance in a liquid medium. The test card includes top and bottom sheets adhesively secured to an intermediate frame member which, together with the top and bottom sheets, defines a filter chamber having a flat filter therein which incorporates a test portion. The test portion of the filter has a binding substrate to which antibodies of the specific substance have been bound. This binding substrate is in communication with a test port. In the method of the invention a substance to be tested is administered through the test port and contains an unknown amount of antigen. After the sample is administered an aqueous solution of enzyme labelled antigen is administered and, subsequently, a liquid substrate is added to cause a color change in the filter below the test port inversely proportional to the amount of antigen contained in the sample administered at the test port.

7 Claims, 2 Drawing Sheets

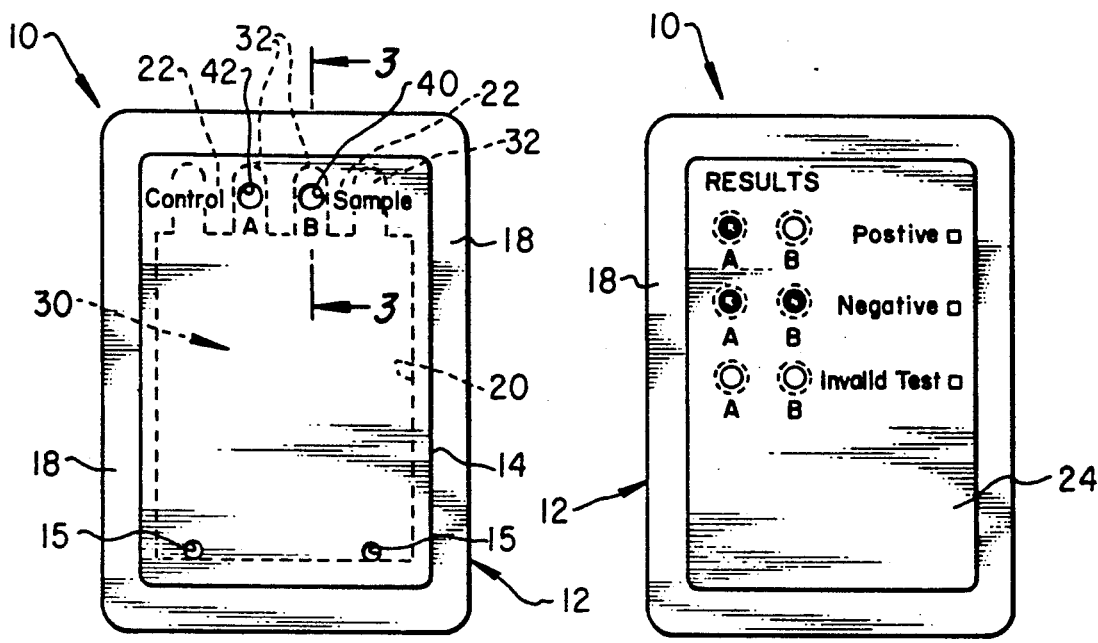
Fig. 1
Fig. 2
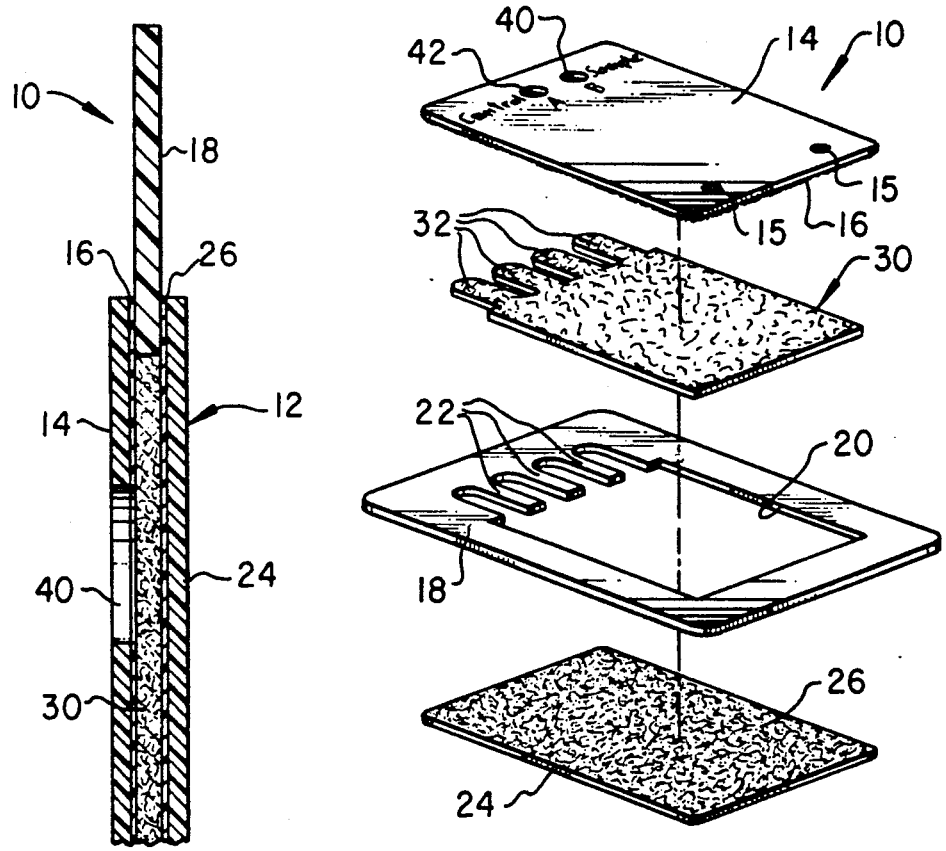
Fig. 3
Fig. 4

TEST KIT FOR DETERMINING THE PRESENCE OF ORGANIC MATERIALS AND METHOD OF UTILIZING SAME

This is a continuation-in-part of our copending Application Ser. No. 775,991 filed Sep. 13, 1985, now U.S. Pat. No. 4,900,663.

BACKGROUND OF THE INVENTION

This invention relates to a colorimetric indicator testing device or card for determining the presence of a specific substance in a liquid medium.

The widespread use of a wide variety of substances in an equally wide variety of environments has made repeated testing for the specific substances necessary in order to control, for example, antibiotic dosages or to determine whether fields which have been treated with various types of organic insecticides are safe for field workers to enter.

Conventional methods of testing entail the drawing or making of a sample of the substance to be tested. For instance, where paraquat is utilized in spraying vegetation, a sample of the vegetation which has been sprayed is taken to the laboratory and a liquid suspension of the paraquat is made which is then subjected to a series of conventional laboratory tests to determine whether the paraquat has been dissipated or whether the amount remaining is so small as to render it safe for workers to enter the paraquat-sprayed field. Naturally, the necessity for remote testing of the specimens of the substance entails consumption of time which delays the harvesting or other necessary treatment of crops.

Similarly, where patients are subjected to large doses of antibiotics, such as neomycin, gentamicin and the like, it is customary to draw blood and to take the blood samples to a hospital laboratory or other laboratories which then make the requisite test necessary to determine the amount of antibiotic present in the blood of the patient. Such remote testing, once again, delays immediate action upon the part of the hospital staff to curb or enlarge the antibiotic dosages as a result of the test indications.

OBJECTS AND ADVANTAGES OF THE INVENTION

To eliminate the delays incident to conventional testing for various types of organic chemicals, antibiotics and the like, we have developed a portable colorimetric testing device which can be embodied in a card which is no larger than the plastic credit card conventionally carried in most individuals' wallets. By the utilization of this card to detect specific substances, it becomes feasible to perform in situ tests at the immediate location Where the substances are to be sampled.

For instance, in the case of paraquat-treated vegetation, a sample of the paraquat is suspended in a liquid medium and immediately applied to the test card and subjected to the series of steps and test substances which will render an immediate indication of both qualitative and quantitative aspects of the extent to which the paraquat remains upon the vegetation.

Similarly, in hospitals where patients are being subjected to massive antibiotic dosages, the blood of the patient can be drawn in a minute quantity and the blood serum extracted by, for instance, the device of co-pending patent application Ser. No. 06/723,162, issued Sep. 29, 1987, entitled "Suspension Liquid Separator". The serum is then immediately administered to the test port of the card to determine the necessity for reducing or increasing the dosage of the respective antibiotic.

It is, therefore, a primary object of our invention to provide a colorimetric testing device which can be utilized at the test site to determine the presence or absence of a specific substance and which eliminates the necessity for remote laboratory testing for the substance.

Another object of our invention is the provision of a colorimetric testing device cf the aforementioned character which can be incorporated in a relatively small package of the approximate size of a plastic credit card, thus facilitating the utilization of the device, the storage of the test results and the supply of the devices to the test site.

A further object of our invention is the provision of a test card of the aforementioned character which is capable, because of its construction and composition, of providing extremely expeditious indications of the presence or absence of the specific substance being tested for.

An associated object of our invention is the provision of a testing device of the aforementioned character which includes a housing or enclosure constituted by top and bottom walls or sheets which are secured to an intermediate frame member to provide a filter chamber. Located in the filter chamber is a flat elongated filter which can be manufactured from a wide variety of different substances such as glass fiber and which is inert to the specific substance and test liquids being utilzied.

An additional object of our invention is the provision, in a testing device of the aforementioned character, of a test area or portion on the filter body which incorporates a binding substrate having a dense application of antibodies for the particular substance being tested linked thereto. Because of the efficiency of the substrate and the dense application of the antibodies to the substrate, rapid results are achieved by the utilization of the testing device in accordance with the method steps of the invention which are alluded to hereinbelow.

A further object of our invention is the provision in a testing device cf the aforementioned character of a control area or portion on the filter body which is juxtaposed to the test area or portion, said control area incorporating the same binding substrate and antibody as the test area and being located in proximity to a control port which is subjected to certain method steps of the invention to provide a control reading which can be compared with the test reading resulting from the administration of the test sample of the substance at the test port and the subsequent application of various test substances and fluids thereto.

An associated object of the invention is the provision of a method of utilizing the testing device of the invention which includes the step of applying or administering a sample of the specific substance being tested suspended in a liquid medium to the test port of the device. When such application or administration at the test port occurs the sample and its liquid medium are immediately drawn into the test area of the filter body and, if there are any antigens present in the liquid medium being administered, they are almost immediately bound to the antibodies supported on the binding substrate.

After the application of the test sample of the specific substance, the next step of the method involves applying an aqueous solution of enzyme labelled antigen at the test port. This solution immediately displaces the sample solution into the filter material with virtually no mixing of solutions.

The next step of the method involves the administration of a substrate solution which will displace the solution containing uncombined, enzyme labelled antigen. The application of the substrate will provide no color indication at all if the antibodies are saturated with the antigens borne in the test substance. On the other hand, if there are lesser amounts of antigens present in the test substance, slight color development will occur. If no antigens are present, complete color saturation will be experienced.

Additional steps of the method entail the utilization of the control port to provide a colorimetric indication of the saturated level of the enzyme test. The achievement of saturation is accomplished by applying the labelled antigen and the color developing substrate to the control area of the filter through the control port. Since the labelled antigens will saturate the antibodies, full color development will result indicating both the operativeness of the test device or card and the maximum color definition which can be expected and with which the test substance color can be compared to determine both qualitatively and quantitatively the presence or absence of the antigens in the test substance.

BRIEF DESCRIPTION OF THE DRAWINGS

Other objects and advantages of the invention will be apparent from the following specification and the accompanying drawings in which:

FIG. 1 is a top plan view of a test card device constructed in accordance with the teachings of our invention;

FIG. 2 is a bottom plan view;

FIG. 3 is an enlarged fragmentary sectional view taken on the broken line 3—3 of FIG. 1; and FIG. 4 is an exploded view showing the various components of the test card of FIG. 1.

DESCRIPTION OF PREFERRED EMBODIMENTS OF THE INVENTION

Figures 5, 6:
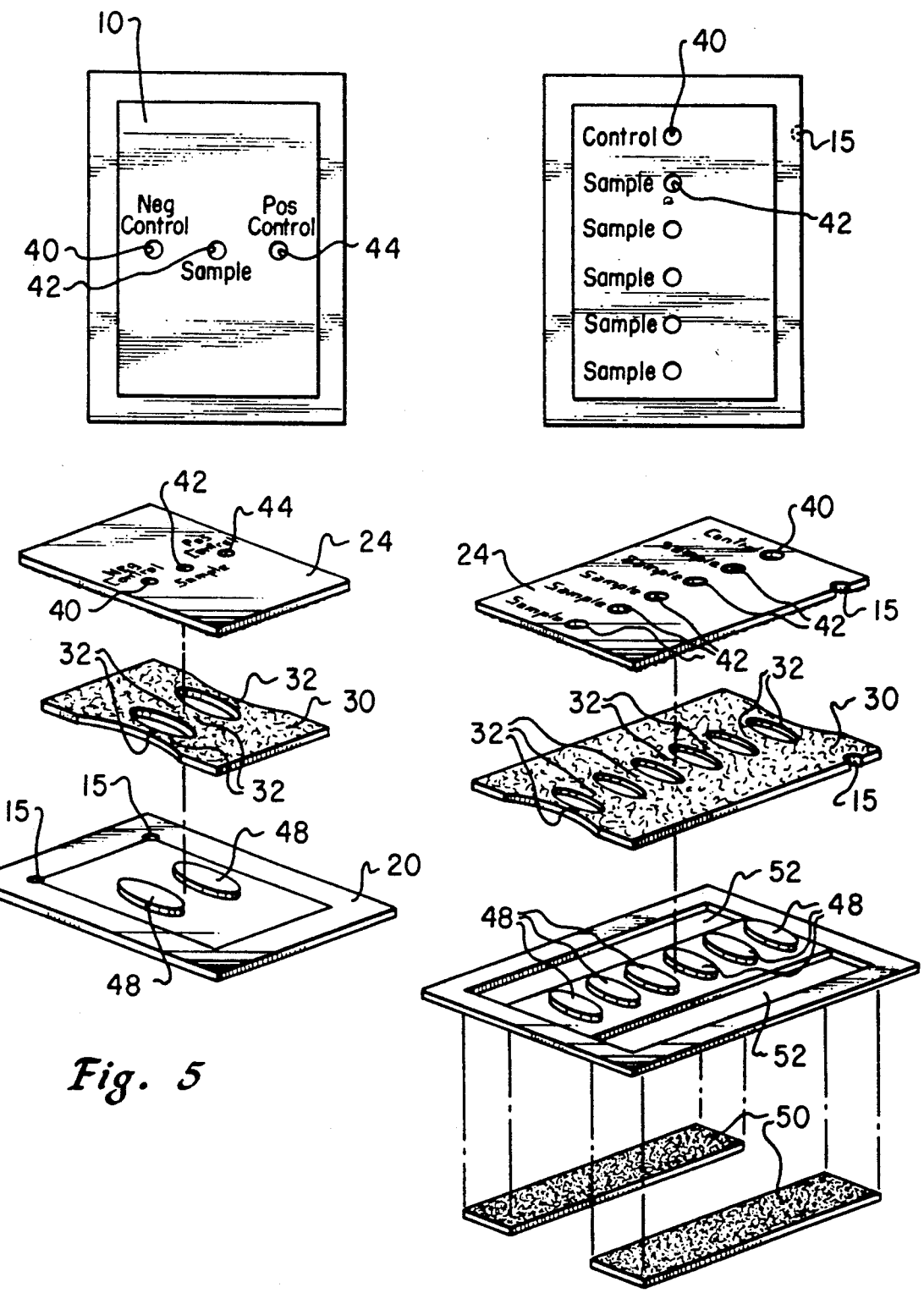
FIG. 5 and 6 are exploded views and a top plan view of two further embodiments of our invention.

Referring to the drawings, we show a colorimetric testing device 10 incorporated in a test card 12 which, as previously mentioned, is approximately the same size as a conventional credit card and of approximately the same bulk. While we show the colorimetric testing device as incorporated, in this embodiment of the invention, in a card, it will, of course, be obvious to those skilled in the art that various embodiments of the invention can be fabricated in different forms without departing from the teachings of the invention.

The test card 12 is of generally rectangular configuration and is constituted by a top sheet 14 fabricated from a synthetic plastic material, such as vinylchloride. Formed in the top sheet 14 adjacent the lower extremity thereof are vent openings 15 which vent the test card in a manner to be described in greater detail below.

The top sheet 14 is adhesively secured to an intermediate frame member 18 which is stamped or otherwise formed from relatively rigid, thin plastic material such as vinylchloride and which incorporates an elongated rectangular opening 20 and has a plurality of fluid isolating or blocking fingers 22 projecting thereinto from the upper portion of the frame member 18.

A bottom sheet 24 of the same material as the top sheet 14 has a pressure-sensitive layer of adhesive 26 upon the upper side thereof and is capable of being secured to the under side of the intermediate frame member 18 thereby.

Located in the elongated rectangular opening 20 of the frame member 18, which serves as the filter chamber of the device 10, is a flat elongated filter body 30, said filter body being formed from compacted glass fibers or the like and incorporating a plurality of upwardly projecting fingers, portions or areas 32 which are insertable in the spaces between the corresponding fingers 22 on the intermediate frame member 18 for a purpose which will be described in greater detail below.

It will be noted that, as best shown in FIG. 1 of the drawings, the vents 15 overlie the lower extremity of the opening 20 constituting the filter chamber and also overlie the lower extremity of the body of the filter 30.

Consequently, as various fluids are deposited at the test sample and control ports, communication of the chamber 20 with the atmosphere facilitates instant separation of the sequentially applied solutions in a manner to be described in greater detail below.

Obviously, the first steps in the manufacture of the test card 12 include the fabrication of the filter body 30 and the intermediate frame member 18, including the projecting fingers 32 on the filter body 30 and the cooperating isolating fingers 22 on the intermediate frame member 18. In addition, the top and bottom sheets 14 and 24 are fabricated and imprinted. The top sheet 14 is provided with the test sample port 40 and the aligned control port 42, legends appearing adjacent said ports to facilitate their utilization.

The filter can be fabricated from a wide variety of filter material and formed from any number of depth-type planar materials capable of entrapping suspension elements or particulates. Exemplary of such a material is glass microfiber material which is available in a range of porosities.

An inherent characteristic of the filter material utilized must be that the filter porosities are interconnected in the plane of the filter. A conventional filter which is capable of entrapping formed suspension elements or particualates, but which is not suitable for the practice of the invention is a planar membrane filter which has porosities connecting its opposite surfaces but offers no pathway for lateral flow generally parallel to and between the surfaces.

In the present construction, the main body of the filter 30 serves to leach or wick liquid from the test and control fingers 32. This insures that subsequent dosages of liquids will be rapidly drawn into the test and control fingers and accomplishes almost immediate operation of the various test liquids applied during the performance of a test on a specific test substance.

In addition, the bottom sheet 24 is imprinted with the legends shown in FIG. 2 to indicate the test results in a permanent manner. Checking the positive box will permanently record the fact that the test was positive; checking the negative box will indicate that the test was negative; and checking the invalid test box will indicate that the test card did not properly operate.

Because of the small size and dimensions of the card, the test results can be readily preserved for permanent record. As indicated in the legends on the bottom sheet 24, when the test sample port B shows no color whatsoever, the test is fully positive. When full coloration is shown at the test sample port B, the test is negative and, as will be explained hereinbelow, when both the test sample port and the control port show no coloration, the test is invalid.

After the imprinting of the top and bottom sheets 14 and 24 in the manner described hereinabove, the reverse sides of the sheets are coated with pressure-sensitive adhesive, as indicated at 16 and 26 of the drawings.

The components of the test kit are assembled prior to the dosing of the test sample and control fingers 32. The filter body is inserted in the opening 20 constituting the filter chamber, and the top and bottom sheets 14 and 24, respectively, are adhesively secured to the perimeter of the frame member 18. After the physical assembly of the test kit 12, the binding substrates are deposited upon the test and control fingers 32 through the test and control ports 40 and 42, respectively. Such binding substrates, of course, must conform to the particular test sample which is the subject of the test.

Typical bacterial binding substrates are Stapehylococcusaureus A and analogous binding bacteria. It is also conceivable that solid substrates, such as microspheroids fabricated from rubber or glass, may be utilized in the filter test and control fingers 32.

It will be noted that additional fingers 32 are provided which, if necessary, can be utilized for ancillary test or control functions.

After the dosing of the fingers 32, which constitute the test and control portions of the filter body 30, the requisite antibodies for the antigen being tested are deposited on the binding substrates of both the test and control fingers and maximum saturation of the binding substrate is achieved.

After the antibodies have been bound on the binding substrate, the test kit 12 is ready for use. Of course, the test kit 12 is appropriately labelled with the name of the test in which it is to be utilized. Consequently, a large number of assembled kits 12 can be maintained in inventory and the substrate antibody combination applied through the test and control ports 40 and 42 when the need for a particular test arises.

It will be noted that the filter body test and control portions, as constituted by the fingers 32, are inserted between the fingers 22 of the intermediate frame member 18, said fingers 22 being impervious to liquid and serving as blocking and isolating means to prevent communication between the test and control fingers 32.

When the top sheet 14 is operatively associated with the frame member 18 and disposed in overlying relationship with the filter body 30, the test and control ports 40 and 42, respectively, are aligned with the bound antibodies on the test and control fingers 32 constituting the test and control portions of the filter body 30.

The antibodies utilized in conjunction with the binding substrate and deposited on the test and control fingers 32 may be purchased from commercial sources for such antibodies oz may be developed by the injection of laboratory animals with selected antigens. In any event, the antibodies must, of course, match with the antigens which are the subject of the test.

For instance, if a test for the presence of paraquat on vegetation is being conducted, the antibodies must be those developed in response to the presence of paraquat antigens.

In making a test for paraquat, a suitable liquid suspension of suspected paraquat residue is administered through the test sample port 40 and, if paraquat antigens are contained in the liquid suspension, they will bind to the antibodies located on the test finger 32.

The antigen will combine with the bound antibody to form a nearly irreversible complex as the test sample wicks through the antibody zone on the test finger 32. The reaction occurs very quickly, within seconds, due to the high concentration of antibody and the sensitivity can be increased by increasing the sample size.

After wicking of the sample is completed, a drop of aqueous solution of enzyme labelled antigen is added to the test port 40. This solution displaces that portion of the test sample liquid which has not been previously displaced by the wicking action into the main body portion of the filter 30. The enzyme labelled antigens bind with any unoccupied antibodies so that the amount of the labelled complex is inversely proportional to the amount of antigen in the test sample.

After the enzyme labelled antigen has been administered through the test port 40, a substrate solution is administered to the test port 40 and displaces that portion of the labelled antigen solution which remains adjacent the port 40. The bound enzyme acts on the substrate to produce a color change which can easily be observed through the test port 40. If no color develops, the indication is that test sample contained sufficient antigen to saturate the antibody.

If complete color development occurs, the indication is that no significant amount of antigen was present in the sample because the labelled antigen has occupied all oz most of the antibody sites.

If an intermediate color change occurs, the indication is that there are antigens present in the sample and the nature of the antigens will determine what decision should be made on the basis of the partial showing of antigens present.

Because of the fact that the lack of color development at the test port is the indication of full saturation of the antibodies by the antigens in the test sample, it is desirable that the control port 42 be accessible to the binding substrate and antibodies present on the control finger 32. This enables the person utilizing the test card to apply the labelled antigen solution at the control port 42. Of course, the labelled antigen will immediately bind with the antibodies and the subsequent application of the color-developing substrate to the control port 42 will result in complete color saturation.

If the antibody labelled antigen combination did not function properly, no colorimetric development would occur indicating that there were defects in the test card 12 which would warrant the discarding of the card 12 and the use of a replacement test card.

Of utmost importance in the functioning of the test kit 12 is the fact that the structure of the card, in its combination of test and control fingers 32 on the large filter body 30 and the vented filter chamber 20, achieves inherent separation of the sequentially applied solutions incorporating, respectively, the test sample, the enzyme labelled antigen and the substrate. The immediate dissipation of the liquid components of the solutions permits the successively applied sample, labelled antigens and developing substrate to function rapidly to produce rapid test results.

In addition, the vents 15 in the top wall 14 materially accelerate the test procedure by establishing atmospheric communication of the lower extremity of the filter body 30 and permitting the successive liquids to flow rapidly downwardly through the filter body 30.

It will be readily apparent to those skilled in the art that the test card and method of using the same of our invention constitute a major advance over the prior art in portability, instantaneous response, built-in control and general utility in a wide variety of applications.

Also of importance is the fact that the density of the antibody applied to the test and control portions of the filter body materially enhances the speed with which the various tests can be performed. Moreover, the presence of the flat filter body and the communication therewith of the test and control portions thereof materially enhances the wicking off of the various solutions applied to the test and control sites, thus materially avoiding the dilution of the various test and other liquids applied during the steps of the method of the invention.

In accordance with another embodiment of the invention, We have discovered that improved results over the card of the type described heretofore are obtained by making certain structural changes in the configuration of the filter body 30 shown in FIGS. 1–4. In FIG. 5, this structural configuration is shown for filter body 30 and it is to be noted that in FIG. 5 the filter body now has the provision Within it of showing at least two sets of projectile fingers 32 leading from the reaction port 40, 42 and 44. This provides so called bi-directional flow of fluids away from the reaction ports. Raised islands 48 separate the reaction sites from one another and vent holes 15 allow proper venting.

Distinct advantages over the uni-directional flow cards indicated in FIGS. 1–4 are obtained. This is due in part to the fact that the fluids can flow now in two directions instead of one, leading to faster wicking. This also enables the use of a smaller hole for the reagent reaction requiring less reagents.

One obtains more flexibility from a card of the present embodiment in that there is a more focused reaction site and the potential of adding a greater volume of liquid material since the wicking action occurs over two reservoirs instead of the one present in the uni-directional flow card. We have found also that there is a subsequent lower background reading when utilizing a bi-directional flow card of the type as shown in FIG. 5.

In some cases it might be desirable to have an added reservoir retention. For example, when several reactions are run on one card of the type shown in FIG. 6, added reservoirs pads 50, may be placed under the filter pad 30 through ports 52 so as to permit the retention of a greater volume of liquid.

The present card also presents more desirable manufacturing economies than the uni-directional flow card since many more tests can be placed on the same card. The card may be hard or soft, of course, as indicated with the uni-directional flow card but with the present embodiment and with the same wicking as is obtained in two ports, it is possible to use six or more ports because the double flow gives rise to a more even distribution of diffused liquid.

Referring now to FIG. 5, it will be observed that filter pad 30 is configured in a way such that projectile fingers 32 are bi-directional with the neck portion thereof being directly under the reaction ports 40, 42 and 44 in top layer 24. It will now be observed that there are two reservoir masses leading from the projectile fingers 32 which communicate with the projectile fingers supplying two separate means to aid in the more rapid wicking of liquid away from the reaction site.

Beneath filter 30 is the plastic template 20 which meets the filter and contains isolation portions 48. These portions separate the reaction chambers in the bi-directional flow mode. If desired, an additional reservoir can be placed intermediate the plastic template and the filter 30 to provide a greater volume of reservoir retention.

Although the above described embodiment in FIG. 5 is a preferred embodiment it is also possible and indeed more preferred under certain circumstances to increase the number of fingers and reaction ports per card to as many as six or more. The mode of operation and the method of preparation is the same for the six as is the two or three shown in FIGS. 4 and 5. For the sake of convenience a diagram has been shown at FIG. 6 of this multi port bi-directional flow embodiment with the operation being self-explanatory.

While We have disclosed the test device as incorporated in a test card, it Will be obvious to those skilled in the art that many different embodiments of the invention can be manufactured without departing from the teachings of the invention or the claims appended hereto.

We claim:

1. A colorimetric indicator testing device for determining the presence of a specific substance in a liquid medium, said testing device comprising the combination of: a housing, said housing including a top wall, a bottom wall and side edges, said top wall having at least one control port and at least one test port therein and said housing incorporating a filter chamber; a flat elongated unitary filter located in said chamber, said filter having a body with a plurality of reservoir portions in fluid flow communication with at least one control portion and at least one test portion for common wicking of liquids in a plurality of directions from said control and test portions; said control and test portions juxtaposed, respectively, to said control and test ports and liquid impervious means between each of said at least one control portion and said at least one test portion.

2. The testing device of claim 1 in which said body of said filter has two reservoir portions for common wicking of liquids in two directions from said control and test portions.

3. The testing device of claim 1 in which said body of said filter has two opposed reservoir portions for common wicking of liquids in two opposite directions from said control and test portions.

4. The testing device of claim 1 in which said edges are constituted by an intermediate frame member, said intermediate frame member defining said filter chamber and said top and bottom walls retaining said filter in said filter chamber.

5. The testing device of claim 4 in which said intermediate frame member incorporate said liquid impervious means which are located between the test and control portions of said filter.

6. The testing device of any one of claims 1 or 5 in which each of said test and control portions of said filter has a binding substrate located therein in juxtaposition to the respective control and test ports and said binding substrate have bound thereto antibody for said specific substance.

7. The testing device of any one of claim 1 or 5 in which reservoir pads are located in fluid flow contact only with said reservoir portions of said flat elongated unitary filter.

* * * * *

UNITED STATES PATENT AND TRADEMARK OFFICE
CERTIFICATE OF CORRECTION

PATENT NO. : 5,240,844
DATED : 8/31/93
INVENTOR(S) : Wie, et al

It is certified that error appears in the above-indentified patent and that said Letters Patent is hereby corrected as shown below:

Column 4, line 17, "al" should be --at--.

Column 5, lines 18 and 19, "Stapehylococcusaureus" should be --Staphylococcus aureus--.

Column 5, line 56 "oz" should be --or--.

Column 6, line 28 "oz" should be --or--.

Column 7, line 21 "Within" should be --within--.

Column 8:
Claim 5, line 2, "incorporate" should be --incorporates--.

Claim 6, line 1 "or" should be --to--.

Claim 7, line 1, "or" should be --to--.

Signed and Sealed this

Eighth Day of March, 1994

Attest:

BRUCE LEHMAN

Attesting Officer     Commissioner of Patents and Trademarks